(12) United States Patent  (10) Patent No.: US 8,061,207 B2
Panetta et al.  (45) Date of Patent: Nov. 22, 2011

(54) SYSTEM AND PROCESS FOR ULTRASONIC CHARACTERIZATION OF DEFORMED STRUCTURES

(75) Inventors: Paul D. Panetta, Williamsburg, VA (US); Marino Morra, Richland, WA (US); Kenneth I. Johnson, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 505 days.

(21) Appl. No.: 12/392,845

(22) Filed: Feb. 25, 2009

(65) Prior Publication Data

US 2009/0193899 A1  Aug. 6, 2009

Related U.S. Application Data

(60) Provisional application No. 61/031,054, filed on Feb. 25, 2008.

(51) Int. Cl.
*G01N 29/07* (2006.01)
(52) U.S. Cl. ............................. 73/622; 73/602; 73/643
(58) Field of Classification Search .................. 73/622, 73/602, 620, 643
See application file for complete search history.

(56) References Cited

U.S. PATENT DOCUMENTS

| 3,660,695 | A | * | 5/1972 | Schmitt | 307/116 |
| 5,375,101 | A | * | 12/1994 | Wolfe et al. | 367/175 |
| 5,503,020 | A | * | 4/1996 | Mandracchia | 73/643 |
| 6,069,430 | A | * | 5/2000 | Tsunoda et al. | 310/180 |
| 6,098,021 | A | * | 8/2000 | Tang et al. | 702/14 |
| 6,502,463 | B1 | | 1/2003 | Clark et al. | |
| 7,657,403 | B2 | * | 2/2010 | Stripf et al. | 702/190 |
| 7,660,197 | B2 | * | 2/2010 | Barolak | 367/35 |
| 7,846,375 | B2 | * | 12/2010 | Gohill et al. | 264/482 |
| 2008/0178679 | A1 | * | 7/2008 | Hirao et al. | 73/643 |

FOREIGN PATENT DOCUMENTS

JP  2011145219  * 1/2011

OTHER PUBLICATIONS

Rosenfeld, M. J., Investigations of Dent Rerounding Behavior, International Pipeline Conference—vol. 1, ASME, 1998.
Alers, George A., EMAT Techniques for Elastic Constant Measurements, Handbook of Elastic Properties, vol. 2, Chapter 9, eds. A. Every and W. Schase, Academic Press, 2000.
Eiber, R. J. et al., The Effects of Dent on the Failure Characteristics of Line Pipe, AGA Catalog No. L51403, May 8, 1981.
Corder, I., et al, EPRG Recommendations for the Assessment of the Resistance of Pipelines to External Damage, EPRG/PRC 10th Biennial Joint Technical Meeting on Line Pipe Research, 1995.

(Continued)

*Primary Examiner* — J M Saint Surin
(74) *Attorney, Agent, or Firm* — James D. Matheson

(57) ABSTRACT

Generally speaking, the method of the present invention is performed by making various ultrasonic scans at preselected orientations along the length of a material being tested. Data from the scans are then plotted together with various calculated parameters that are calculated from this data. Lines or curves are then fitted to the respective plotted points. Review of these plotted curves allows the location and severity of defects within these sections to be determined and quantified. With this information various other decisions related to how, when or whether repair or replacement of a particular portion of a structure can be made.

9 Claims, 12 Drawing Sheets

OTHER PUBLICATIONS

Thompson, R. B., Physical Principles of Measurements With EMAT Transducers, Ultrasonic Measurement Methods, Physical Acoustics, vol. XIX, 1990.

Thompson, R. B., et al., Ultrasonic Methods, Handbook of Residual Stresses, Chapter 7, pp. 149-178, The Fairmont Press Inc. Lilburn, GA, 1996.

Kobayashi, Michiaki, Acoustoelastic Theory for Finite Plastic Deformation of Solids, JSME International Journal, Series I, vol. 35, No. 1, 1992.

Kobayashi, Michiaki, Acoustoelastic Theory for Plastically Deformed Solids, JSME International Journal, Series 1, vol. 33, No. 3, 1990.

* cited by examiner

Bulged pipe, x60, 20" diameter, yield strength = 60K psi

SYSTEM AND PROCESS FOR ULTRASONIC CHARACTERIZATION OF DEFORMED STRUCTURES

This invention was made with Government support under Contract DE-AC05-76RL01830 awarded by the U.S. Department of Energy. The Government has certain rights in the invention.

FIELD OF THE INVENTION

The invention relates generally to ultrasonic assessment methods and systems. More particularly, the invention is a system and process for ultrasonic characterization of deformed structures such as deformed containment vessels, pipelines, bridges, rail systems, vehicles, and the like.

BACKGROUND OF THE INVENTION

Assessing and maintaining integrity of aging structures are of primary importance. Specifically, there is a need to detect and characterize degradation to infrastructure to allow for proactive measures to be taken to minimize potential losses of life and damage to property and natural resources. Examples of the various needs for information vary by particular industry. However, the underlying theme in nearly all questions is answering this fundamental question: "is this component fit for continued service at the current capacity, or does the capacity need to be reduced, or do repairs or replacements need to be made immediately?" These questions arise in a variety of contexts ranging from the oil and gas industry to transportation to civil engineering. Accurate characterization of deformed and damaged pipelines, and real-time detection of tampering or detrimental impacts to a portion of a pipeline is of particular importance to the world's oil and gas pipeline infrastructure. Either immediate or delayed failure of a pipeline can occur as a result of mechanical deformation or damage of the pipeline due to a variety of factors ranging from subsidence to earth movement as well as other causes. Immediate failure may occur, for example, when construction equipment punctures the pipeline and produces a leak at the time of damage. However, mechanical deformation and damage more frequently provide an initiation site for crack formation and delayed failure. Unreported deformation, for example, can result in delayed failure due to either slow crack growth through the thickness or hydrogen-stress cracking of the cold worked and strain-aged steel. Often these delayed failures are caused by fatigue cracks which grow due to cyclic stressing at deformed and damaged locations. Furthermore, structural integrity assessment standards are based on the level of strain present in the structure (e.g., a pipeline) either due to mechanical deformation and/or damage induced by other causes. Measurements required to make these assessments can be particularly difficult in situations where structures that need to be analyzed are large in size and/or are difficult to remove or access. Of particular need is the ability to accurately assess, in situ, the extent of any deformation and/or damage, as well as strain in a pipeline structure that may have been deformed and/or damaged by various intentional, accidental, or natural acts such as sabotage, construction equipment impacts, or earthquakes. Current methods for determining the degree of deformation and/or damage (including, e.g., strain) in various regions of a closed structure such as a pipeline can be complicated and expensive and in some cases impossible due to a variety of factors including, but not limited to, microstructure texture variations in the materials that make up the structures and the difficulty in separating these effects from damage. What is needed therefore is a system and method that can utilize ultrasonic techniques to perform quantitative and/or qualitative analyses of features such as strain, deformation, and damage on structures to obtain information relating to the extent of deformation and/or damage such as dents, bends, bulges, and other deformations. The present invention provides a method and enables a system that allows for such measurements to be made in an effective, efficient, and functionally accurate way. Additional advantages and novel features of the present invention will be set forth as follows and will be readily apparent from the descriptions and demonstrations set forth herein. Accordingly, the following descriptions of the present invention should be seen as illustrative of the invention and not limiting in any way.

SUMMARY OF THE INVENTION

The invention in one aspect is a method for determining damage to a structure. Determining and assessing damage by the method includes the steps of: determining two principal polarization directions of an acoustic wave traveling in a structure; propagating and receiving test waves along a length of the structure oriented at, or near, the principal directions; plotting preselected data related to the test waves; calculating a birefringence value(s) from the propagated test waves; determining a strain value(s); plotting the strain value(s) and the birefringence value(s) to create a strain-birefringence plot; fitting an appropriate regression line or curve to the strain-birefringence plot; and predicting damage to the structure by comparing data calculated from the strain-birefringence plot with a baseline component determined from the first plot.

The invention accurately assesses severity of damage to a structure and accurately determines the current state of material properties in the damaged region. The material properties can be used as inputs into computation mechanics models that predict operating requirements such as burst strength and maximum operating pressure, as well as in the prediction of remaining useful life. The key parameters needed are the residual stress and plastic strain.

Generally speaking, the method of the present invention is performed by making continuous ultrasonic scans at preselected orientations along the length of the material being tested. Data from these scans is then plotted together with various parameters calculated from this data. Lines or curves are then fitted to the respective plotted points. Review of these plotted curves allows the location and severity of defects within these sections to be determined and quantified. With this information, various other decisions related to how, when, or whether repair or replacement of a particular portion of a structure can be made.

In one embodiment, the present invention includes a novel application of birefringence stress/strain measurement methods to provide a fast, continuous spatial mapping of damaged portions or locations or regions in a metallic structure. The invention can be readily implemented for use with existing in-line-inspection tools or PIGs, and sensors such as those currently used to assess railroad rails and bridge components. The present invention allows pipeline damage, including strain, to be determined automatically in a reliable and efficient manner. In another embodiment of the invention, the method is employed in measurement of pipelines and assessing damage thereto. While this specific embodiment is described hereafter it is to be distinctly understood that the invention is not limited thereto but may be variously embodied and configured according to the needs and necessities of the user. The typical utilization of the present invention in a pipeline configuration begins by first determining a fast polarization direction and a slow polarization direction of acoustic waves traveling in the wall of a pipeline relative to a pipe axis of symmetry (axial and hoop directions). This can be done in a variety of ways but is most easily done by initially varying the orientation of an acoustic wave-creating device, such as an Electromagnetic Acoustic Transducer (EMAT), in proximity to the internal or external surface of the structure and making various scans. The EMAT generates the acoustic (ultrasonic) signal at the surface of the material thereby eliminating the need for coupling gels, which also eliminates negative effects such as irreproducible coupling and liftoff. The invention also measures material properties of the scanned structure including thickness. In a preferred embodiment, the EMAT does not contact the surface that is scanned. By performing these scans, symmetry of the material, and fast and slow directions (i.e., that the acoustic wave is polarized relative to the axial and circumferential (hoop) directions of the pipe) can be determined. Once these directions have been determined, orientation of the sound wave producing devices (e.g., EMATs) is typically fixed so that at least one transducer emits a signal in a first direction and the same (or at least one other) transducer emits a signal in a second direction with nearby polarizations. After these device components have been fixed into a preselected configuration and orientation, baseline data (e.g., about the structural integrity) can be obtained by moving these generally fixed components (EMATs) along a length of the structure (e.g., pipe) where the structure is in a stress- or strain-free, or otherwise undamaged, state. Then scans (i.e., sending transmissions out and receiving transmissions back and measuring various characteristics regarding these transmissions) are performed at preselected intervals of the structure being scanned. These intervals may be varied depending upon evaluation criteria or other needs of, or inputs entered by, the user, to allow for an appropriate balance between the rate of a scan and specificity of a scan to be achieved. For general scanning, a longer interval between scans may be desired, while in a more detailed scan, interval between scans may be preferably decreased.

The invention provides an estimate of the stress and strain in a structure that has been deformed or damaged. The change in acoustic (ultrasonic) velocity or the change in a velocity combination (e.g., birefringence as described further herein) due to deformation of, or damage in, a structure are used to determine the level of strain in the structure. These velocity (and velocity combination) measurements are independent of thickness. For example, the birefringence, a thickness independent feature, is a result of measuring velocity of two independent shear waves in the scanned structure polarized in different directions. The invention orients polarizations of the shear waves and scans the structure along lines with a fixed polarization at or near each of two material symmetry axes. Resultant velocities are used to calculate the shear wave birefringence. The polarizations can align with the material symmetry axes to provide a maximum velocity and a minimum velocity, at a minimum, based on the material texture of the scanned structure, as well as the stress and strain. By doing this, various material properties and characteristics of the structure (e.g., a pipe) can be obtained. For example, thickness, and thickness-independent measurements of plastic strain in a damaged structure can be determined. As scans of a structure are collected, preselected information obtained from these scans, e.g., time of flight, distance, and/or amplitude is recorded and plotted. Typically, each designated or preselected parameter is plotted separately in a plot. Timing of the plotting may vary and need not be done contemporaneously with the receipt of information obtained from these scans. Plotting of data points may also take place at various intervals or cumulatively depending upon the needs and necessities of the user. In addition, various other pieces of information related to the structure being analyzed are also calculated from this raw data and preferably plotted. Examples of such calculated parameters include, but are not limited to, thickness of a pipe, the shear wave birefringence (i.e., the percent difference between the fast and slow mode for shear waves polarized along the principal axes of the material or structure), the strain on the pipeline, and/or other desired or selected parameters. Exact methods for calculating these features may be suitably varied according to the needs and necessity of a user. Examples of various methods are provided hereafter in the detailed description.

After obtaining this baseline information, the suspect damaged portions, or target sections of the pipe are similarly analyzed by performing scans proximate to or within these suspect damaged regions. The data obtained from these scans is also similarly processed and plotted as described above. Specific parameters or characteristics that are measured and/or calculated from the data obtained from these scans may be varied according to the needs and necessities of the user. In one embodiment, a calculated birefringence and amplitude are utilized.

Once these calculated parameters have been plotted, a curve or line is fitted to the data points, for each set of values. Comparing these curves of plotted data then provides a visual array that demonstrates how test values move away from baseline data. Location and magnitude of these variations provide information that demonstrates the location and severity of the damage to the structure being examined. Comparative studies based on a direct measurement of material properties rather than thickness have shown that the results obtained using this method correlate well with more burdensome and costly methods while doing so in a faster more efficient manner. Therefore, enabling devices that employ these methods can be effectively deployed. Since this method has increased efficiency particularly as compared to other methods, smaller devices that require less energy can be utilized to accomplish the calculations required by this method.

This arrangement provides a variety of advantages over the devices and methods that are taught in the prior art. By focusing scans on preselected portions of the pipe, the entire inner portion of the pipe need not be scanned and surveyed. This allows for increased speed in moving the device along the pipe and also limits the number of data points that are collected thus allowing for more efficient and quick computational results, and requires less reduced electrical power than other methods or devices. Devices that employ the present method may be used on pipe PIGs or saddle PIGs that obtain measurements of the pipe from either the inside or the outside of the pipe, respectively. In addition the present invention may be used with pipes that are full or empty and which have mixed gas and liquid phases and materials within these pipes.

In another embodiment, a structure (e.g., pipe) can be scanned using several scanning lines by either moving EMAT sensors along the circumference of, or laterally along, the structure. Scanning speed can also be increased (e.g., by a factor of two) by employing two (or more) EMATs with shear waves polarized at each of two material symmetry axes. In one configuration, the scanning system is comprised of a phased array. In another embodiment, a single EMAT sensor comprised of 2 coils oriented approximately 90 degrees relative to the other can be utilized to excite waves at two polarizations during a single scan. No limitations are intended.

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Various advantages and novel features of the present invention are described herein and will become further readily apparent to those skilled in this art from the following detailed description. In the preceding and following descriptions I have shown and described only the preferred embodiment of the invention, by way of illustration of the best mode contemplated for carrying out the invention. As will be realized, the invention is capable of modification in various respects without departing from the invention. Accordingly, the drawings and description of the preferred embodiment set forth hereafter are to be regarded as illustrative in nature, and not as restrictive.

TERMS

Figure 1:
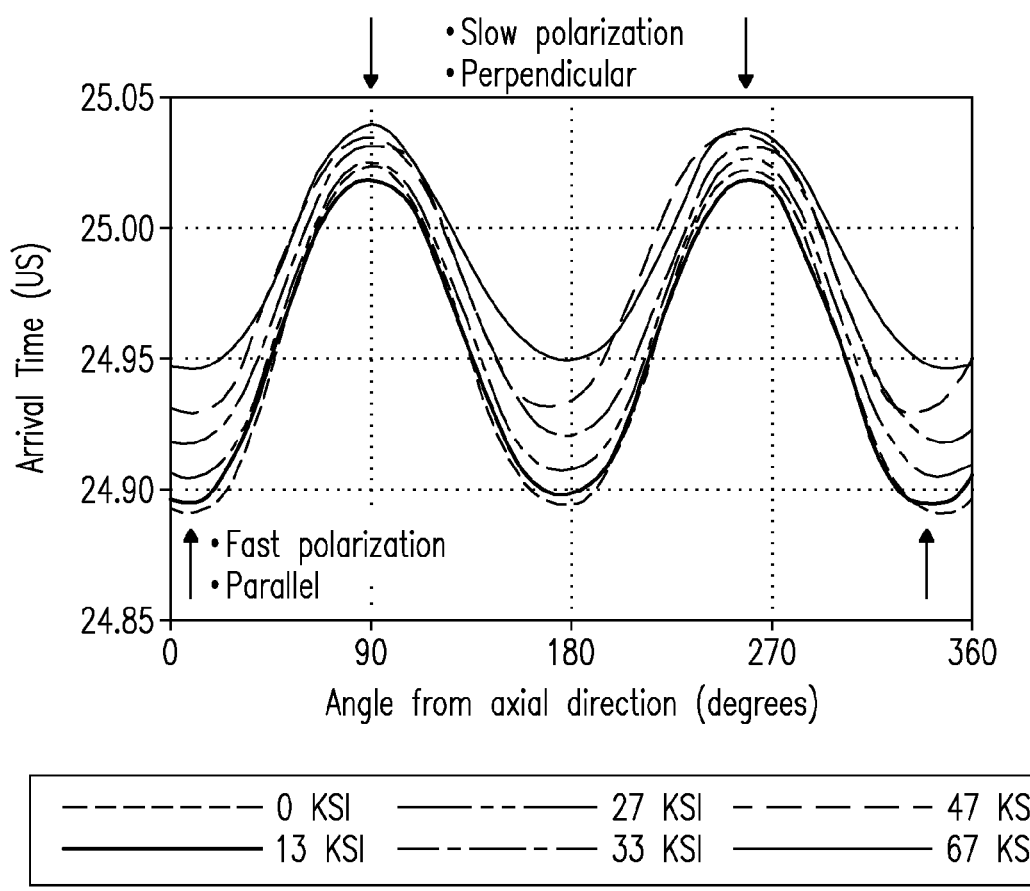
FIG. 1 shows time-of-flight profiles for travel of sound waves in a section of pipe scanned at preselected angles according to a preferred embodiment of the method of the invention.

The following terms are used herein.

Deformation: Change in mechanical dimensions (size or shape) of an object from an applied force. Plastic or Elastic movement, or separation, in a structure or material.

Damage: Any amount of elastic or plastic strain that results from a deformation of a material. Damage can be deemed inconsequential or consequential based on assessments and evaluations of the structure or material.

Stress: Force per unit area (F/A). Typical units in mechanical applications are kips-per-square-inch (ksi), where 1 kip=1,000 pounds of force per square inch.

Nominal Yield Stress: Magnitude of an applied stress (F/A) needed to initiate deformation of a structure (yield point).

Residual Stress: Stress residing in a structure after it has been deformed or damaged.

Strain: Change in length $\Delta L(\ )$ of a physical structure as a consequence of an applied stress, divided by the original length $[(\Delta L/L_0)]$ as a percent (%). As an example, a bar of steel one-inch in length that is deformed to a length of 1.1 inches experiences a strain value of 10%.

Plastic Strain: Deformation of a structure that is permanent after a stress is released. Also termed "plastic deformation".

Effective Strain As used herein, effective strain ($\epsilon_p$) is synonymous with "equivalent" strain and "resultant" strain, and is given by Equation [1]:

$$\epsilon_p = \sqrt{\frac{2}{3}(\epsilon_1^2 + \epsilon_2^2 + \epsilon_3^2)} \quad [1]$$

Here, $\epsilon_1$, $\epsilon_2$, and $\epsilon_3$ are individual strain measurements associated with the material, or pipe symmetry, axis.

"Lift off": Distance of the sensor from a surface of a structure being examined. The lift-off distance can increase or decrease as the sensor examines the structure.

DETAILED DESCRIPTION OF THE INVENTION

The present invention is a method and a system for determining the quantity and/or quality of damage to a structure, including, but not limited to, e.g., pipelines, bridge components, and structural components. The invention can detect and characterize damage in a structure due, e.g., to earth movement or impact. The invention overcomes obstacles associated with static, single-point measurement approaches deployed in the conventional art by orienting the polarization of shear waves along material symmetry axes and then scanning a structure along lines with, e.g., a fixed polarization at each of the two principal, orthogonal material symmetry axes. The invention can be used to scan continuous metallic structures, including, but not limited to, e.g., pipelines, bridges, tanks, fuselages, and support structures (e.g., I-beams, metal sheets and plates). In one embodiment, the invention employs ultrasonic measurements to identify a damaged region and to characterize a degree of deformation. The measurements are sensitive to plastic strain and residual stress in the damaged structure. This technology can be deployed for characterizing pipelines which have, e.g., been dented due to third party damage, and for pipelines that have been bent or stretched due to earth movement or impact. The following description provides one example of one preferred embodiment of the present invention. From this description it will be noted that various modifications, alterations and substitutions may also be made without departing from the spirit of the invention as set forth in the scope of the claims listed hereafter. Accordingly, the present description of the preferred embodiment should be seen as illustrative only and not limiting.

In one embodiment of the present invention, damaged sections of pipeline were measured utilizing birefringence stress/strain measurement methods; data were correlated to provide fast, data efficient, spatial mapping of damaged regions in the pipeline. While this particular embodiment is described hereafter, it is to be distinctly understood that the invention is not limited thereto but maybe variously embodied according to the needs and necessities of a user. FIG. 1 is a graph showing typical time-of-flight (arrival time, μsec.) for travel of sound waves measured with polarization angles of from 0 degrees to 360 degrees offset from the starting axial direction position, at applied stresses in a section of pipeline from 0 ksi (baseline) to 67 ksi. Once direction-determining polarizations are placed in the structure, baseline (i.e., background) time-of-flight data and distance measurements are obtained, calculated, and plotted for each of two measurements (e.g., fast and slow, axial and hoop, ordinary and extraordinary). If needed, thickness of the material can be calculated from time-of-flight values measured at each of two polarizations (e.g., axial and hoop), and the average of the two results can be maintained. This thickness determination can be made utilizing standard handbook values of elastic modulus, or speed of sound, for the piping material, as well as equations related to shear wave velocity. In addition to, but independent of, this thickness calculation, the shear wave birefringence is also calculated. Shear wave birefringence is determined by dividing the difference between the fast and slow (or ordinary and extraordinary, or parallel and perpendicular, or axial and hoop) time-of-flight values by the average time-of-flight value, as given by Equation [2]:

$$Birefringence = \frac{T_\perp - T_\parallel}{(T_\perp + T_\parallel)/2} \quad [2]$$

Here, ($T_\parallel$) is the time of flight measured in a first polarization direction and ($T_\perp$) is the time of flight measured in a second polarization direction. The first polarization can be perpendicular to the second polarization, but directions are not limited thereto. Moving point averages (e.g., N-point averages where $N \geq 3$) of birefringence values can be used, e.g., to smooth large numbers of data points in continuous scans of structures being examined.

Figure 2:
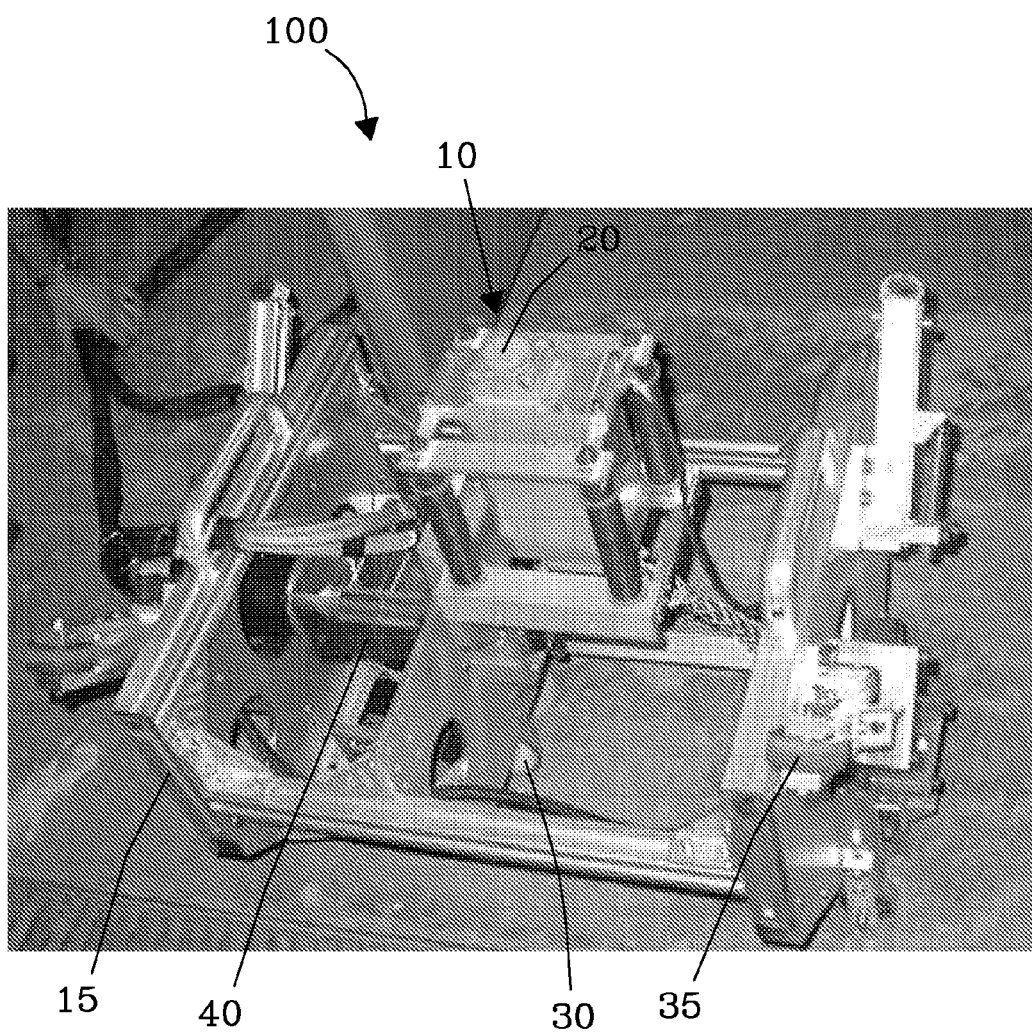
FIG. 2 is a perspective view of a scanning device used in conjunction the invention for examining the interior surface of a pipeline.

FIG. 2 shows an exemplary scanning device 100 used in conjunction with the invention that provides a continuous structural birefringence measurement over a continuous length of damaged and undamaged structures. In the figure, the exemplary device includes a single electromagnetic acoustic transducer (EMAT) 10 available commercially (e.g., Innerspec Technologies, Lynchburg, Va., USA) mounted onto a rudimentary cart 15, but is not limited thereto, as described further herein. In the exemplary device, the EMAT is configured with a 1.5 inch coil 20 coupled with a permanent magnet or an electromagnet (not shown) that delivers shear waves oriented along preselected directions (e.g., hoop and axial directions) of the surface of the structure being scanned. The scanning device provides continuous time-of-flight measurements in various scan modes over a continuous length or portion of the damaged structure along the preferred polarization directions. The instant scanning device 100 includes an encoder wheel 30 that establishes the revolutions, portions of revolutions, or the timing that triggers the pulser/receiver 25 to deliver shear waves for the scanning measurements. One or more guide wheels 35 can be used to stabilize the scanning device during external or internal measurements of the structure being scanned to provide a suitable precision. Other allied or additional components may be incorporated into the scanning device as will be understood by those of ordinary skill in ultrasonic arts. No limitations are intended.

For example, computers, software, stepper motors (e.g., for scanning under incremented or motorized control), gages (e.g., dimension, pressure, temperature, or other gages), scales (e.g., for orientation or rotation), sensors, and like devices and components can be incorporated.

Figure 3A:
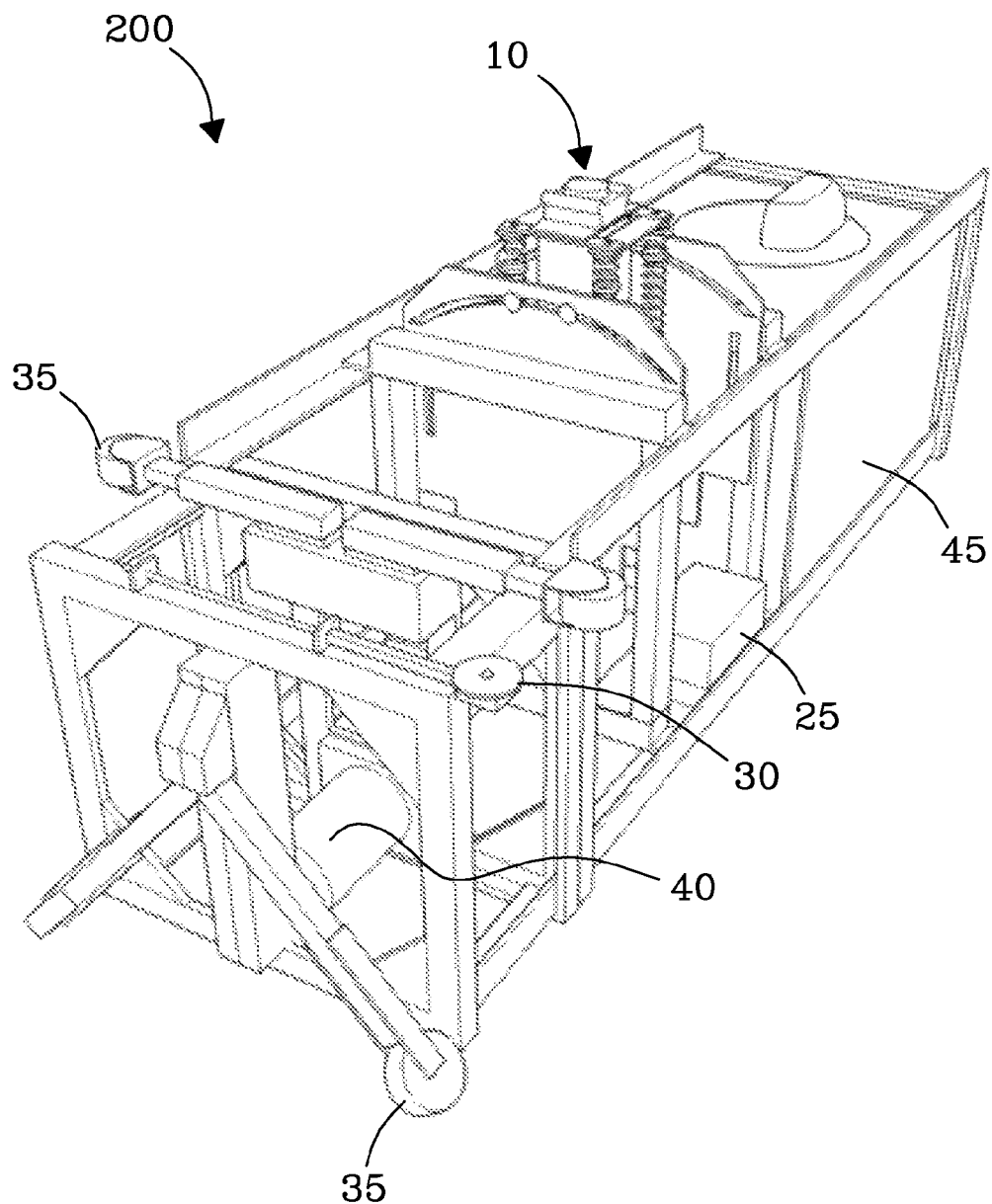
FIGS. 3a-3b present two views of another scanning device for examining the interior surface of a pipeline.
Figure 3B:
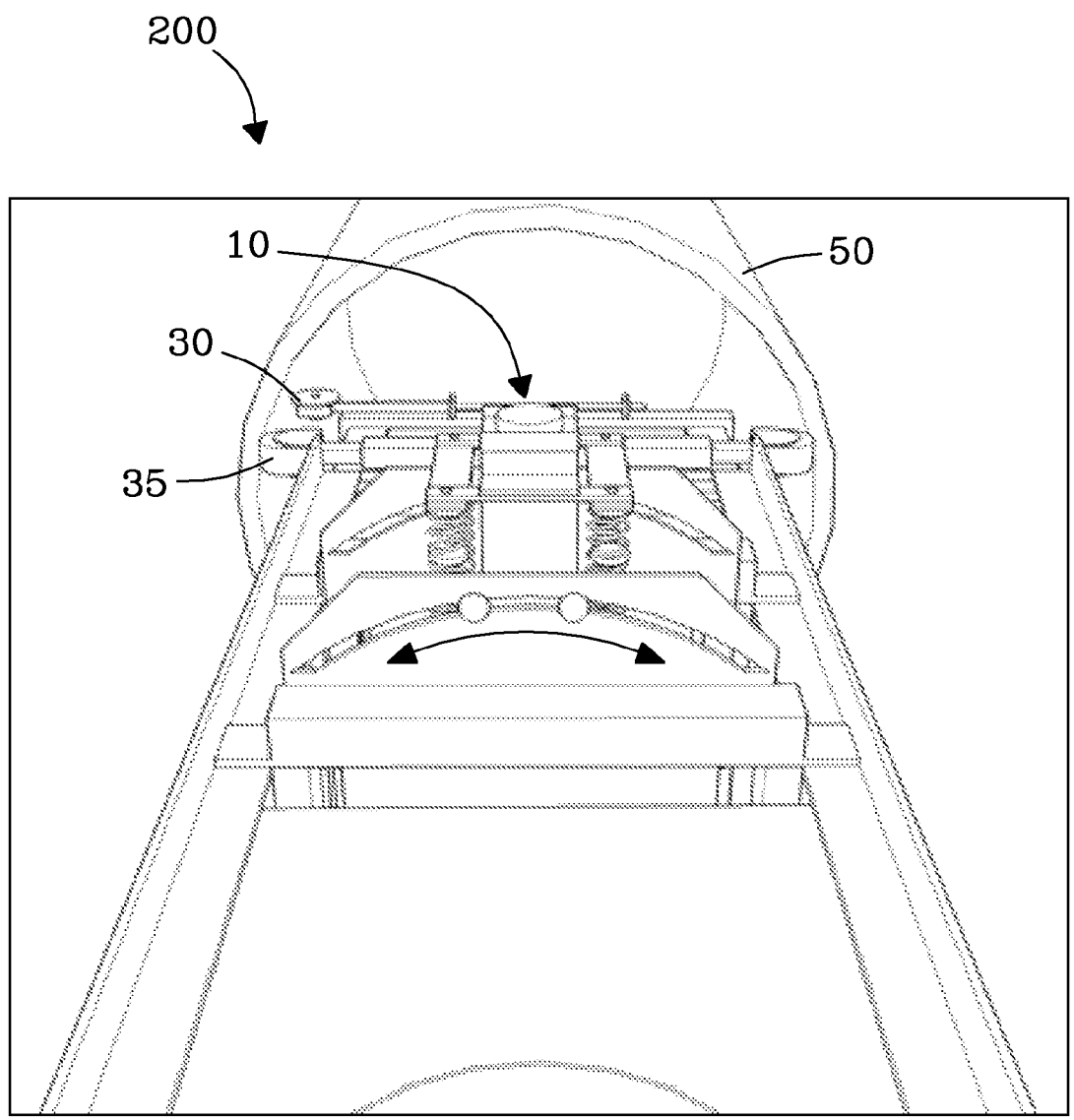

FIGS. 3a-3b present two views of another scanning cart device 200 and configuration that provides continuous structural birefringence measurements over an entire (complete) portion or a continuous length of a pipeline surface. The present invention assesses pipeline damage and allows strain to be determined in a reliable and efficient manner. FIG. 3a is a perspective view of scanning device 200, which is configured for examination of the interior surface of a damaged pipeline. In the figure, the exemplary device has dimensions (5'3" Length×15" Width) and is configured to provide continuous structural birefringence measurements of the entire internal surface, or a continuous segment, of the pipeline. The scanning cart device 200 includes a stepper motor 40 that can rotate the sensor 10 for circumferential (hoop) scans and/or provide forward or rearward movement of the cart or sensor along the length of the pipeline being scanned. A pulser/receiver 25 pulses the EMAT 10 to deliver shear waves along the preselected polarization directions during the scanning measurements and also receives and measures the acoustic signal for the scanned structure. An encoder wheel 30 electrically couples to, and triggers, pulser/receiver 25 at preselected revolutions and increments of revolution (e.g., ½-revolution) of the encoder wheel. A computer 45 interfaces to, and provides control of: the encoder wheel, the pulser/receiver, the EMAT, and also collects time-of-flight and associated sonic data that provide for continuous structural birefringence measurements of the entire surface of a continuous length or portion of the pipeline surface being scanned. Guide wheels 35 stabilize the scanning cart in the pipeline at the selected polarization orientations. The exemplary scanning device includes 9.5 inches of manual adjustment in the hoop direction to orient the device in preparation for scanning of the interior surface of the pipeline. No limitations are intended. All components as will be implemented by those of skill in the art in view of the disclosure are within the scope of the invention. FIG. 3b is an end-on view of scanning cart device 200 positioned at the opening of a 24-inch diameter pipeline (e.g., natural gas pipeline) that was scanned and structurally assessed by the present invention. Other pipe diameters can be scanned as well. Thus, no limitations are intended. The dented pipeline was scanned from the interior along the axis of the pipeline under remote control. For scans along the length of the interior, the EMATs scanned the axial (length) direction at different locations. Measurements were also collected in the circumferential (hoop) direction at these same locations. The EMAT generated a wave which traveled through the thickness of the pipeline, but is not limited thereto. For example, the acoustic wave can also travel along the surface, or in the volume of the pipe wall in either the axial or the hoop directions. Data were collected every 0.1" along the axis at a speed of 5 inches per second, which parameters are not limited. Two scans were used to acquire data for each wave polarization, resulting in a scanning time of 3 minutes, which produced 4800 data points located 0.1" apart. The result was a fast scan time and an overlap in position that provided for spatial averaging. This embodiment allowed motion relative to a pipeline coordinate system of approximately 50+ feet linearly (i.e., axial direction) and ±60 degrees circumferentially (i.e., hoop direction).

While a particular embodiment of a scanning device has been described, it is to be distinctly understood the invention is not limited thereto but may be variously embodied according to needs of the user or particular testing conditions. For example, the invention can be readily incorporated into various existing scanning device configurations such as pipeline PIGs and saddle yokes. In addition, EMAT sensors can be positioned to scan the inside or outside of a pipeline or structure either under motorized control or by hand. In addition, arrays of sensors can to be deployed either within (inside) or without (outside) the section of pipeline to be analyzed to provide birefringence measurements for an entire surface of a continuous length or portion of the pipeline surface being scanned, as described further herein. In addition, the cart can be motorized as described herein to provide automated scanning of the inside or exterior of a pipeline using the EMAT sensor(s) positioned in the axial direction or the circumferential direction. In the following embodiment, the cart can be moved forward and backward under motor control such that the EMAT sensors provide for axial measurements. The EMATs can also be mounted to be rotated collectively in a circular direction under motor control, or be prepositioned at preselected angles or locations, to conduct circumferential (hoop) measurements.

Figure 4:
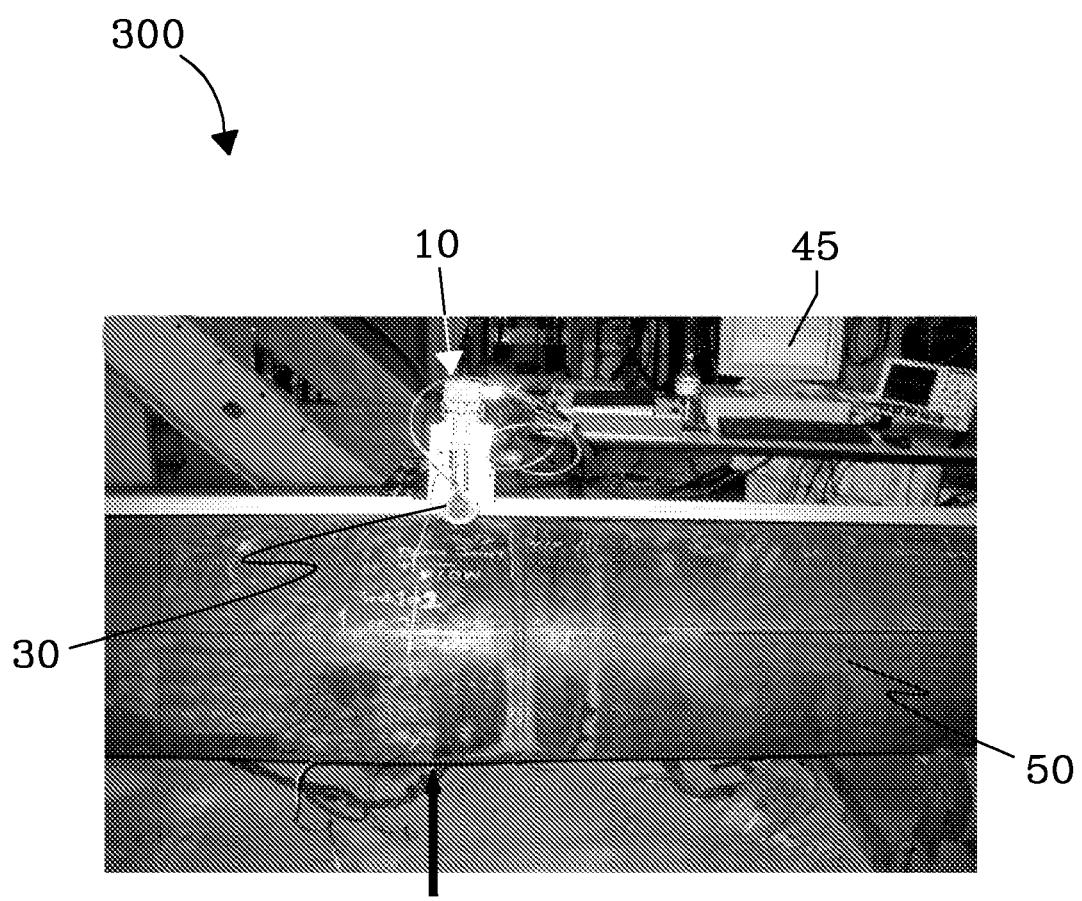
FIG. 4 is a view of an external pipeline surface scanned in accordance with the invention.

FIG. 4 shows another embodiment of a scanning device 300 used for scanning the exterior surface of a damaged structure. In the figure, an exemplary damaged structure is shown, e.g., a pipeline (20-inch diameter X60 pipeline) that was scanned in conjunction with scanning device 300 configured at a minimum with an EMAT sensor 10 (described previously herein in reference to FIG. 2), an encoder wheel 30; and a computer 45, which provided for continuous measurement of the external surface of the damaged (bulged) pipeline. The pipeline included a weld. Sections of the pipeline in front of, and past, the weld (designated Pipes 1 and 2, respectively) were scanned. In an exemplary test, an aluminum track was attached that ran along the external surface of the pipeline to keep the EMAT sensor oriented properly for scanning. In another embodiment, scanning measurements were conducted under motorized control utilizing a single EMAT sensor, but is not limited thereto. Yield strength of the pipeline was determined to be 60K psi.

Figure 5:
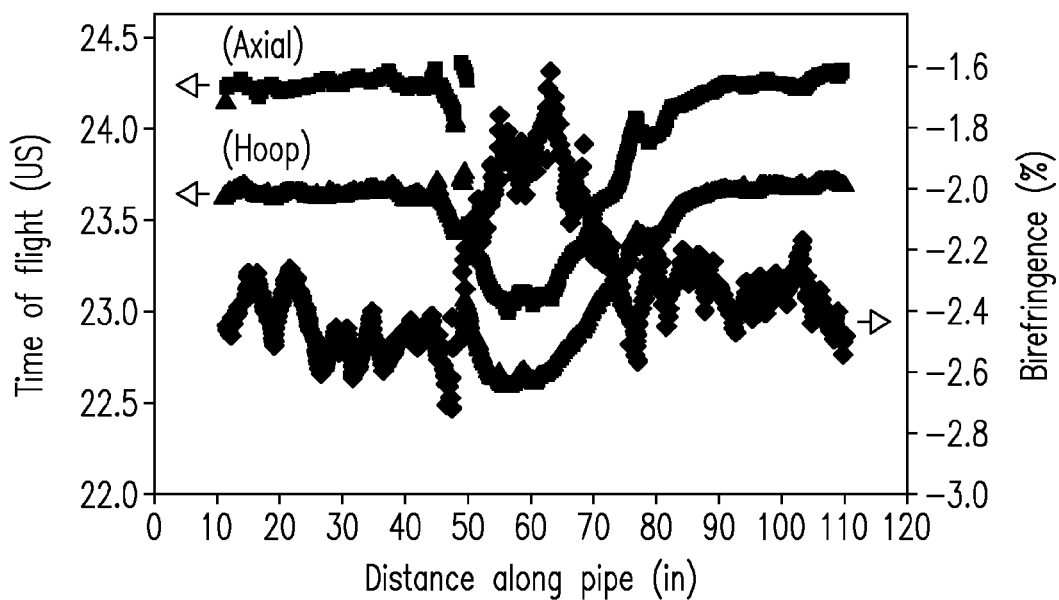
FIG. 5 plots time of flight values and birefringence values as a function of the distance for a section of damaged pipeline.

FIG. 5 plots time of flight (μsec.) values against birefringence (%) values (thickness-independent) calculated from continuous shear-wave data collected using (coil) polarizations oriented in, or near, the parallel ($T_∥$) (axial) and perpendicular ($T_⊥$) (hoop) directions along the length axis of the damaged pipeline. Exemplary choices for polarization direction are not intended to be limiting. In the figure, moving point averages are shown for time of flight and birefringence values, respectively. Results show a decrease in time of flight values and a large increase in birefringence at a distance of between about 50 inches and about 75 inches in the pipeline, which correlated with the structural damage (e.g., bulge) or defect in the actual pipeline at that location. Birefringence values can also be plotted and correlated against thickness (i.e., deterministic) measurements in a structure.

Figure 6:
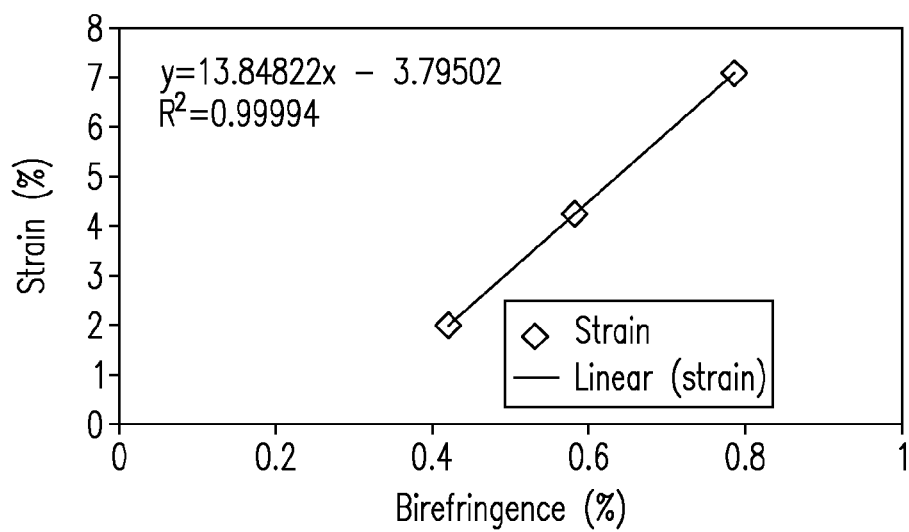
FIG. 6 correlates strain and birefringence values for a section of damaged pipeline.

Strain (e.g., plastic strain) in a particular structure can be determined in a variety of ways, including, e.g., ultrasonic measurements of the deformed structure; deterministic (e.g., thickness and circumferential) measurements; elemental data modeling; or from mathematical relationships such as the Kobayashi theory [(M. Kobayashi: "Acoustoelastic Theory for Finite Plastically Deformed Solids", JSME (Japan Society of Mechanical Engineers) International Journal, Series I, Vol. 33 (3) 1990 and M. Kobayashi: "Acoustoelastic Theory for Finite Plastic Deformation of Solids", JSME International Journal, Series I, Vol. 35 (1) 1992] incorporated herein. Birefringence as a function of strain can also be correlated using birefringence values in a strain free region, and birefringence values in increasingly strained specimens and structures up to and including a maximum strain. Strain-birefringence data for the examined structure can then be correlated using a curve-fitting routine (e.g., least-squares) or other regression analysis to obtain an equation that predicts strain for birefringence values measured or determined at other locations in the sample or material under test. FIG. 6 presents a typical strain-birefringence plot for an examined structure or test specimen (e.g., pipelines, bridge beams, uniaxial tensile specimens, or other structures). In the figure, ultrasonic strain values (% deformation) are plotted against birefringence (%) values for the test sample (e.g., bulged pipe). Strain in a scanned structure at other locations of the structure or pipeline can then be predicted using birefringence values using, e.g., a strain-birefringence plot, from which the amount of strain.

Figure 7:
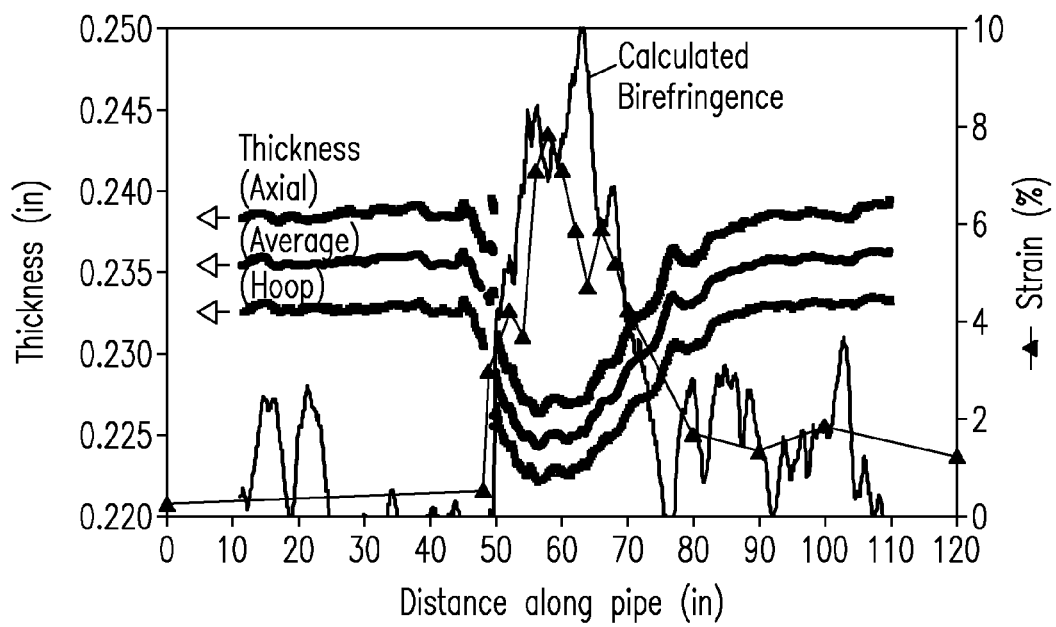
FIG. 7 plots thickness and strain as a function of distance for a section of damaged pipeline.

Thickness and strain can also be correlated for a scanned structure (e.g., pipeline). FIG. 7 is a plot that shows thickness and strain as a function of distance in a pipeline scanned by the present invention. In the figure, effective strain, determined from dimensional measurements (i.e., thickness and circumference measurements), and ultrasonic birefringence (%) are plotted as a function of distance along the pipe. Thickness is also plotted, as determined from individual axial polarization and hoop polarization scans, and the average thickness as determined from combined axial and hoop polarization scans, respectively. Results demonstrate that the invention can effectively determine thickness and strain in a damaged structure. In particular, results reveal a section of pipeline where structural damage is evident and where remediating measures may be desired. The graph shows structural damage (i.e., a bulge) at a distance along the pipeline of between about 50 inches and about 75 inches. In particular, there is a dramatic increase in the birefringence, an increase in effective strain, and a decrease in thickness. These results correlate with time-of-flight and birefringence data shown previously herein (see FIG. 5).

Figure 8:
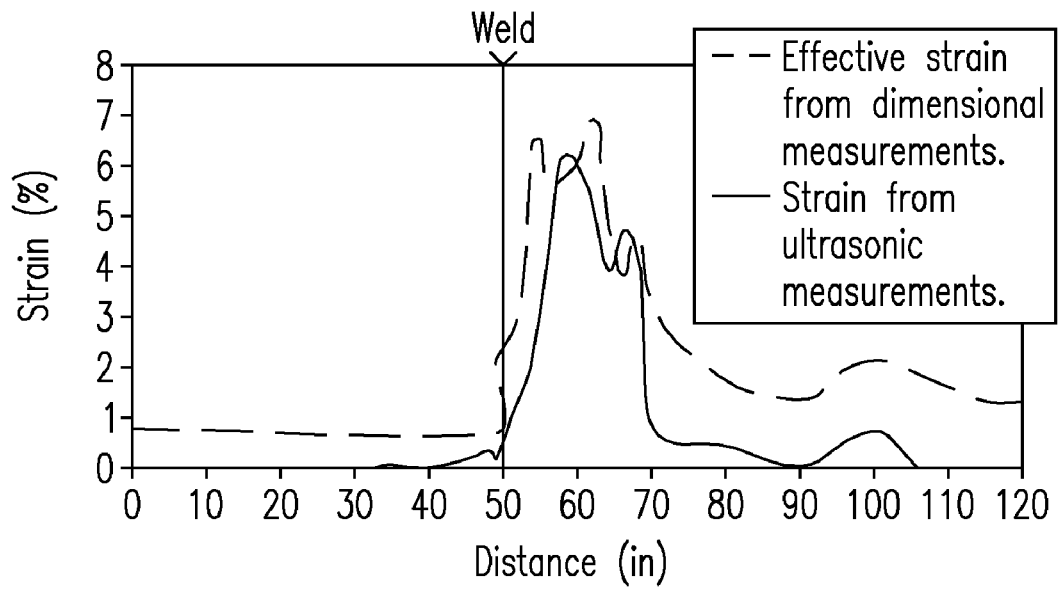
FIG. 8 plots strain and effective strain values as a function of distance for a section of damaged pipeline.
Figure 9:
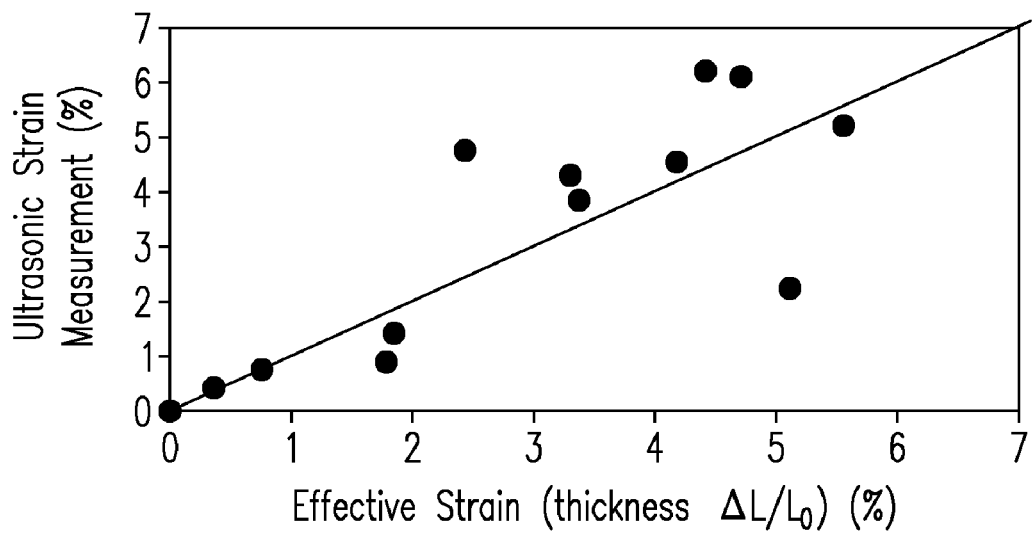
FIG. 9 plots ultrasonic strain as a function of effective (resultant) strain from measurements of a section of damaged pipeline.

FIG. 8 plots strain values (%) as a function of distance along the damaged pipeline. Strain was correlated with birefringence values determined from scanning measurements. Effective strain values ($ΔL/L_0$)—calculated from dimensional measurements of the circumference and thickness—and the ultrasonic birefringence as a function of position along the pipeline axis are plotted. Results show that the strain predicted from shear wave birefringence measurements of the scanned structure correlated well with the effective strain from deterministic measurements. And, strain measurements also correlated well with deterministic measurements in the highly strained (e.g., bulged) region where the birefringence increased dramatically. Results compare favorably with published uniaxial tensile test data for pipeline steels. The increase in birefringence that occurs with increases in strain demonstrates that birefringence is directly related to the degree of plastic strain in these specimens. Because ASME regulation codes for pipeline operation are based on strain in a pipeline, not thickness, ability to provide thickness-independent measurements is important. Ability to measure acoustic properties independent of the thickness is significant, as the degree of residual stress and plastic strain in the damaged structure due to the mechanical damage need to be assessed, not the thickness of the pipeline. Deformed metals (e.g., in pipelines) naturally thin under a tensile load, and ultrasonic time-of-flight measurements are affected by such thinning. To assess the strain in pipelines described and measured herein, thickness dependence was removed from the ultrasonic time-of-flight measurements by combining specific time-of-flight measurements, i.e., the ultrasonic birefringence measurements calculated from Equation [2]. Birefringence is dependent on the stress/strain crystallographic texture and elastic moduli of the metal in the walls of the pipelines. Thus, birefringence changes from location to location based on changes in stress and strain in the pipelines. FIG. 9 plots ultrasonic strain (%) predicted from ultrasonic measurements of birefringence as a function of the effective in-plane strain ($\Delta L/L_0$, calculated from the measured thickness strain) for a section of examined pipeline. This plot confirms that the strain estimate (i.e., based on the ultrasonic birefringence) generally follows the trend that is associated with the measured strain. An algorithm can be created from this data and used as a calibration. The calibration can be based on measurements from a limited number of locations, or from laboratory calibrations, or from theoretical equations that correlate the birefringence as a function of strain, e.g., as a prediction process. The regression equation can then be used to predict the effective strain for birefringence values calculated from measurements collected from the examined structure. High precision ultrasonic measurements were collected along several scan lines in straight and bent pipelines that had a variability of less than 0.5%. Based on these measurements, the minimum detectable strain level in the deformed regions of the pipeline was approximately 1% to 2% strain with an uncertainty of ±1% strain (FIG. 7). In general, thickness independent measurements can be used to assess the degree of strain in pipelines that have been damaged due to subsidence (sinking) or other movement during, e.g., weather-induced landslides, earthquakes, or other sources. Measurements can also be used to determine equivalent strain in pipelines that have been bulged due to over pressurization. In addition, results show that thickness-independent ultrasonic measurements can be used to determine if bending performed in the field is within specifications. Results can also be used to help meet specific structure codes (e.g., ASME, API, ASTM, and the like) for pipeline operation, e.g., to assess maximum operating pressure in deformed and/or damaged structures to determine when to replace pipelines or to lower operating pressures.

Other parameters such as amplitude (i.e., the intensity of sound) may also be used to locate and assess damage. For example, plots of amplitude as a function of distance along the pipe axis and hoop directions can be used to quantify the extent of damage (e.g., length and width of a dent) for one or more locations of a particular structure. Changes in amplitude from the baseline condition are used to assess the damage, including, e.g., 1) using the full-width-at-half-maximum method, 2) using the width at some percentage of the maximum value based on a calibration or other suitable calibration method, or 3) using the amplitude peak height method. No limitations are intended. Amplitude variations can be attributed to "lift off" of the sensor from the pipeline surface. The extent of "lift off" in the axial and hoop directions can be used to determine size and shape of, e.g., a dent.

Size or extent of physical dents (whether hidden or visible) can also be determined using changes in birefringence (i.e., from baseline). Changes in birefringence typically indicate presence of texture, stress, and strain variations. Changes or deviations in birefringence values from baseline can be used as a qualitative measure of the amount of stress and strain in a deformed or damaged portion (e.g., dent) or region, and can also be used to rank the severity of the deformation or damage. In general, the greater the deviation of the birefringence from baseline, the more severe the dent and the greater the degree of strain in the structure. Thus, by considering variations in amplitude and/or birefringence, the relative severity of dents can be ranked and compared with benchmark values.

Figure 10A:
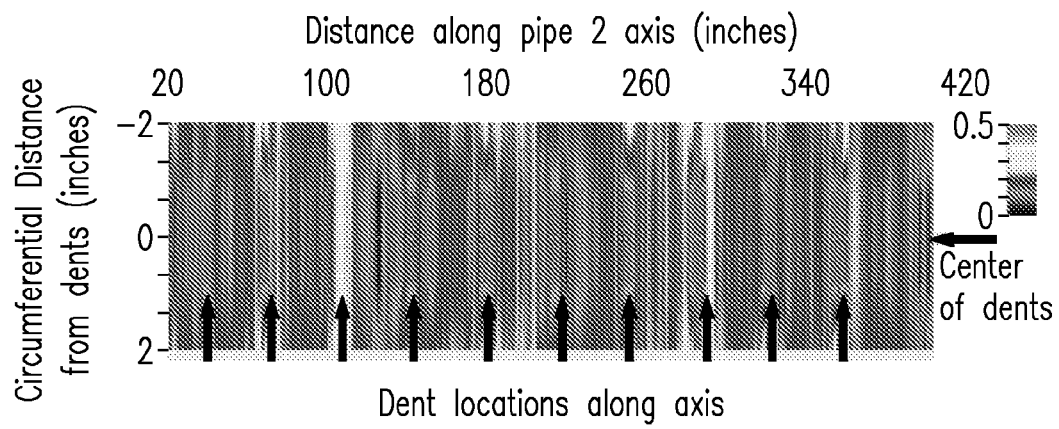
FIGS. 10a-10b compare amplitude and birefringence data collected from ultrasonic scans as a function of distance along the axis of a damaged pipeline.
Figure 10B:
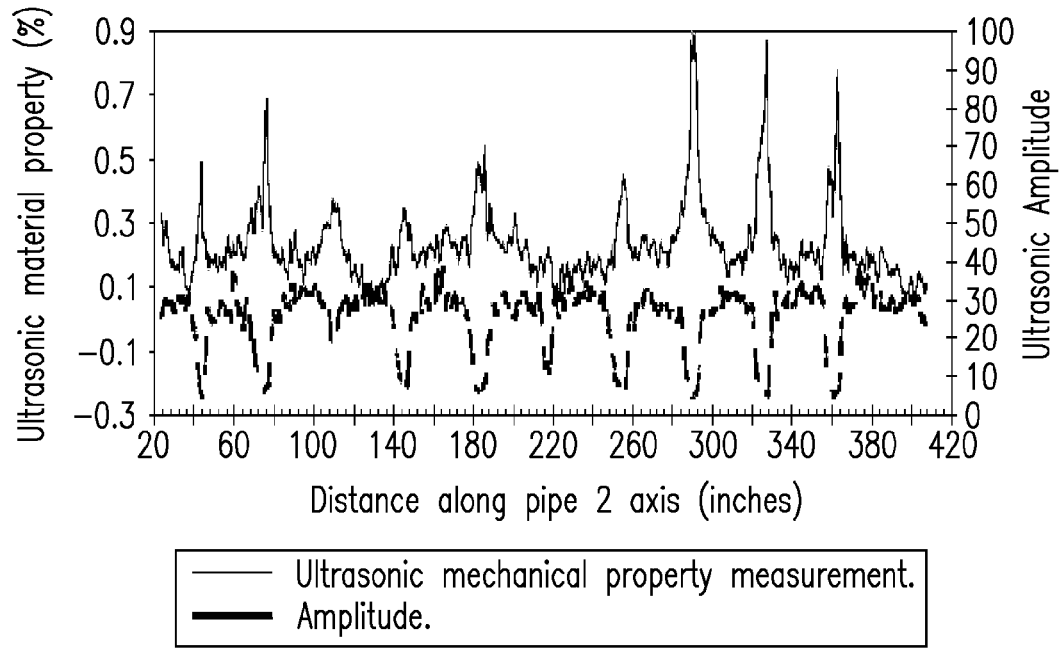

FIGS. 10a-10b compare amplitude and birefringence data from ultrasonic scans collected as a function of distance along the interior surface of a damaged (i.e., dented) pipeline. Dents were introduced at preselected locations from top dead center along the axis of the pipeline. FIG. 10a shows a topographical representation of the amplitude of the ultrasonic signal from multiple scans collected along scan lines positioned at circumferential (hoop) distances from top dead center ("0" position) of from +2 to −2 inches. Arrows show the position of dents introduced into the pipeline prior to initiation of scan measurements. FIG. 10b compares shear wave birefringence and ultrasonic amplitude data as a function of axial distance along a continuous section of the damaged (dented) pipeline. Data shows that the ultrasonic birefringence and amplitude data (FIG. 10b) are closely aligned with the locations of dents (FIG. 10a) in the damaged pipeline. Data further show that the dent locations can be determined whether the scan measurements are taken in close proximity to the dent or whether measurements are taken off-center from the damage location. The shear wave birefringence was also used to determine the dent severity at each location. Two dents introduced into the pipeline were used as calibration (benchmark) dents to develop the ultrasonic ranking for severity. The benchmark for severity was based on the size, shape, and depth of these dents. For ultrasonic measurements, the spatial duration of the change in birefringence values at a selected damage location was an important ranking parameter. In particular, the greater the magnitude of the birefringence above baseline, and the greater the duration of the deviation from baseline in both the axial and circumferential directions, the greater the severity ranking. These shear wave birefringence measurements were collected as a measure of the mechanical damage, and were independent of the thickness of the pipeline. TABLE 1 lists results.

TABLE 1

Severity ranking for dents introduced into a steel pipeline, as determined by the invention compared to a control.

| LOCATION: | 1 | 2 | 3 | 4 | 5 | 6 | 7 | 8 | 9 | 10 | 11 |
|---|---|---|---|---|---|---|---|---|---|---|---|
| Distance (inches) | 42.25 | 73.25 | 109.25 | 144 | 183 | 217 | 253 | 289.5 | 325 | 360.5 | 397 |
| SEVERITY RANK | | | | | | | | | | | |
| Benchmark | 1 | 2 | 1 | 3 | 2 | 1 | 2 | 3 | 2 | 3 | 0 |
| Invention | 1 | 2 | 1 | 2 | 3 | 1 | 2 | 3 | 2.5 | 3 | 0 |

Results detected 100% of hidden dents and correctly assessed degree of the deformation and severity at 7 of the 9 reporting locations. Ranking from this blind test compared favorably with benchmark values. Ultrasonic shear wave birefringence values measured 3.5 inches from top dead center from the damage locations (e.g., dents) in the pipeline retained sensitivity necessary for characterizing damage severity. Thus, measurement locations are not limited.

The aforementioned scanning arrangements provide a variety of advantages over devices and methods taught in the prior art. For example, by focusing scans on preselected portions or sections of a pipeline or structure, the entire structure (or, e.g., the inner portion of the pipeline) need not be scanned and surveyed. Location-specific or spot-specific scanning and analysis allows for increased speed in moving the scanning device along the pipeline, which can also reduce and limit the number of data points that need to be collected. Efficient and quick computational results are obtained, which reduces electrical power usage of remotely powered tools, as compared to prior art methods or devices. The present method also employs devices that may be used on pipeline or saddle PIGs to obtain measurements from either the inside or the outside of the structure being examined, respectively. In addition, the present invention may be used to scan pipelines that are full or empty, or which contain mixed gas and liquid phases and materials within the pipelines. Sensors and electronics described herein can also be configured for use on small pipelines (e.g., ~4" diameter or less) and are also conducive for attaching to PIGs and robot inspection tools that are used to detect corrosion, as well as stress-corrosion cracking. The present invention also provides the capability to determine strain in both bent and bulged pipelines. It also allows the ability to detect, classify, and characterize dented pipelines in the field. For example, measurements can be performed under remote motorized control from either the inside or outside of a pipeline or other metal structure to assess pipeline or structural integrity. In addition, the present method also could be used in the integration of the nondestructive determination of structural damage with computational mechanics models that predict operating parameters such as maximum operating pressure for decisions on replacing or repairing a damaged section or region of a structure. The present invention also provides an increase in spatial coverage and speed compared to other prior art methods while maintaining functional efficacy. In exemplary experiments with a single transducer measuring 1.5" in diameter, results demonstrate that approaches with a scanning system described herein increased the speed of data acquisition by a factor of approximately 210 and enables the incorporation of this measurement technique into scanning devices such as pipeline inspection PIGs. This embodiment of the invention also lends itself well to implementation with pipelines because standard manufacturing processes including, e.g., plate rolling, bending to form a cylinder, seam welding, and hoop expansion result in natural alignment of the metallic grains in the pipeline, whether parallel or perpendicular to the pipeline axis, depending on the rolling and transverse directions of the various plates during the construction processes. One embodiment of the present invention thus allows for continuous scanning without the need to baseline the sensor orientation at each pipeline segment as a result of the preferential grain alignment and overall spatial coverage. Principal stresses in a pressurized pipeline also align typically in (with) the axial and hoop directions, allowing the stress effects to be included in the stress and strain estimates obtained from birefringence measurements. Typical variations in the alignment of fast and slow polarization directions relative to a pipe axis (e.g., a pressurized pipe) are shown, e.g., in FIG. 1. Fixing the sensor polarization orientations also eliminates moving parts in the scanning device and dramatically reduces the data set required for each measurement location along the pipeline axis. In addition, data post-processing can be automated with hardware and software. Additionally, because of the low profile nature of EMAT technology, EMATs can be used to scan over long distances and can be easily added to compliment sensor packages of existing PIGs. Large-scale structural deformations including, e.g., structural bending due to landslides, or structural deformations due to over-pressure (e.g., bulging) can also be assessed.

While the invention has been described herein in conjunction with a single EMAT device utilizing a single coil, the invention is not limited thereto. In addition, while scans of pipelines described herein were performed with polarizations at fixed angles (e.g., in, or near, the hoop and axial directions, respectively, each approximately orthogonal to the other), in some circumstances (e.g., at pipeline junctions), it may be necessary to track the ultrasonic signal, e.g., in real-time, due to changes in the thickness of a material being scanned, which can alter the preselected directions for the fast and slow polarizations. Thus, while the aforementioned description has been provided, it is to be distinctly understood that the invention is not limited thereto but may be variously embodied and configured according to the needs and necessities of a user. No limitations are intended.

Figure 11A:
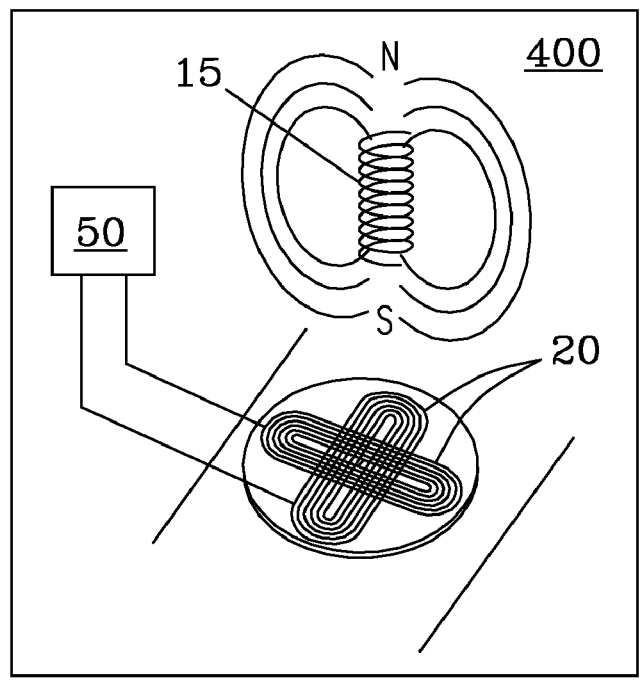
FIG. 11 shows a sensor configuration that employs two EMAT coils that couples with a magnet for determination of shear wave birefringence, according to an embodiment of the invention.
Figure 11B:
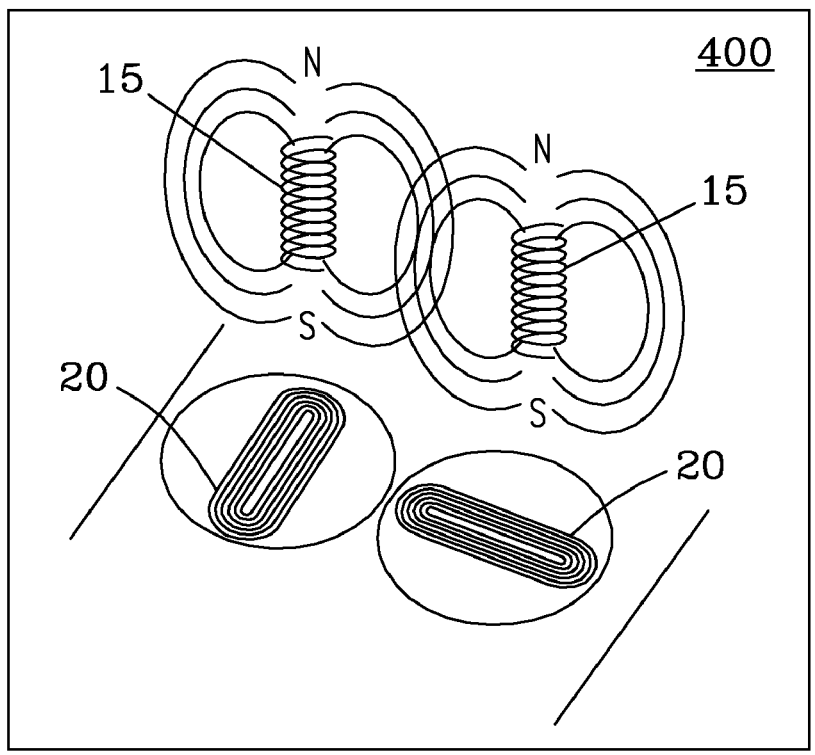

New sensor and coil designs that incorporate more than one EMAT sensor or coil are envisioned that can provide acoustic data of a continuous structure, e.g., in a single continuous scan. FIG. 11a illustrates a new EMAT sensor 400 according to an embodiment of the invention that includes two (2) EMAT coils 20 in an overlapping coil design. Each coil 20 is oriented in a preselected polarization direction or at a preselected, non-limiting, angle as described herein for scanning of a structure. In scanning systems that incorporate this design, scan speed can be increased, e.g., by a factor of two using two EMAT coils with shear waves polarized at each of two material symmetry axes. Scans of the surface of the structure can then be performed in a single continuous scan, e.g., for determination of shear wave birefringence. In the instant configuration, both coils 20 are coupled to a single magnet 15 (e.g., an electromagnet or a permanent magnet) to provide a magnetic field for each polarization. Electromagnets are preferred due to the small footprint for space-limited applications, but are not limited thereto. In addition, this coil combination allows close nesting of multiple sensors 400 that can improve data resolution and provide improved surface area coverage. A switching device 50 (e.g., relay) and related components can be used to switch and power each respective coil at preselected times and/or distances along the measured structure, e.g., in an alternating manner. Alternatively, multiple channel electronics devices can be used, as will be understood by those in the electronics arts. No limitations are intended. In another embodiment illustrated in FIG. 11b, two single magnets 15 can be coupled, e.g., in an offset position design, to two or more single coils 20 in a single sensor 400 device, each coil 20 being positioned at a different orientation to provide continuous data along preselected angles, polarizations, or directions in a single continuous scan of a structure. The offset coil design does not offer the same nesting capacity as does the overlapping design (FIG. 11a) and therefore may not exhibit the same resolution. However, the offset design does not require electronic switching between coils and magnets. Thus, the expected electronic switching overhead is negligible. In addition, this design can be implanted with both permanent magnets and electromagnets for each polarization orientation. Additional configurations (e.g., structured arrays) described further herein that employ more than 2 coil/magnet combinations coupled together are also envisioned that provide a continuous scan of spatially advanced or complex structures. New sensor array designs are described hereafter that can also be deployed to provide scanning measurements of a continuous structure. Magnetic fields produced by EMAT sensors, and orientations of the magnetic fields, are described, e.g., by Clark et al. (U.S. Pat. Nos. 6,311,558, and 6,502,463) which matter is incorporated herein in its entirety. Magnetic fields can be employed including, but not limited to, e.g., pulsed magnetic fields, constant magnetic fields, and uniform magnetic fields, including combinations of these types. Thus, magnetic fields illustrated in FIGS. 11*a*-11*b* are intended only to illustrate the presence or use of magnetic fields, but is not intended to be limiting as to specific orientation. As described herein, magnetic fields can be generated in conjunction with a permanent magnet or an electromagnet, including, e.g., pulsed electromagnets or DC electromagnets. Placement of electromagnets and permanent magnets is also not intended to be limited.

Structured Arrays

Figure 12A:
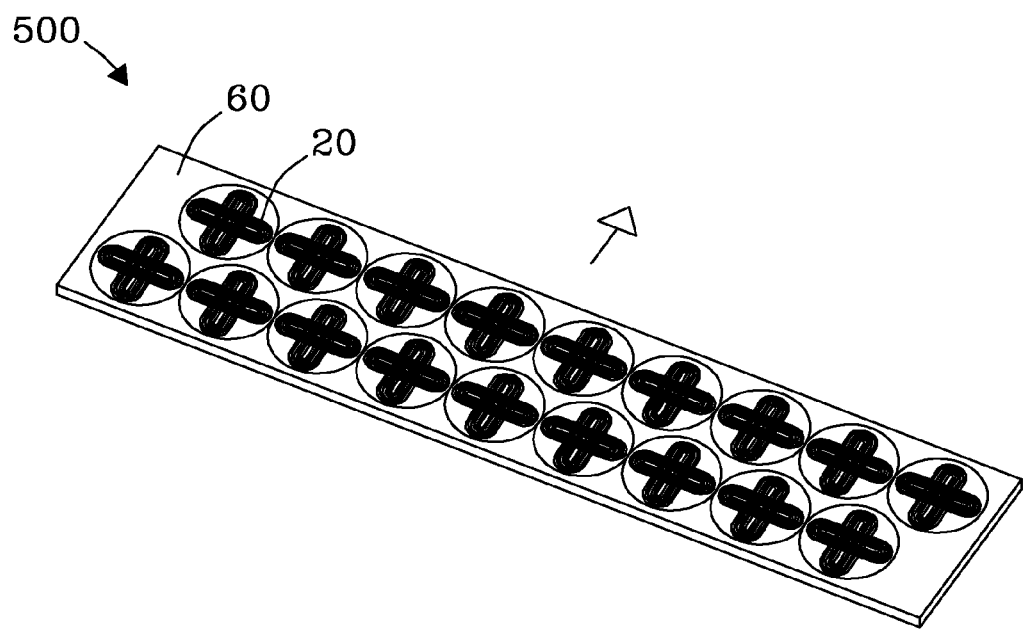
FIGS. 12a-12c shows three configurations of an EMAT sensor array, according to three different embodiments of the invention.
Figure 12B:
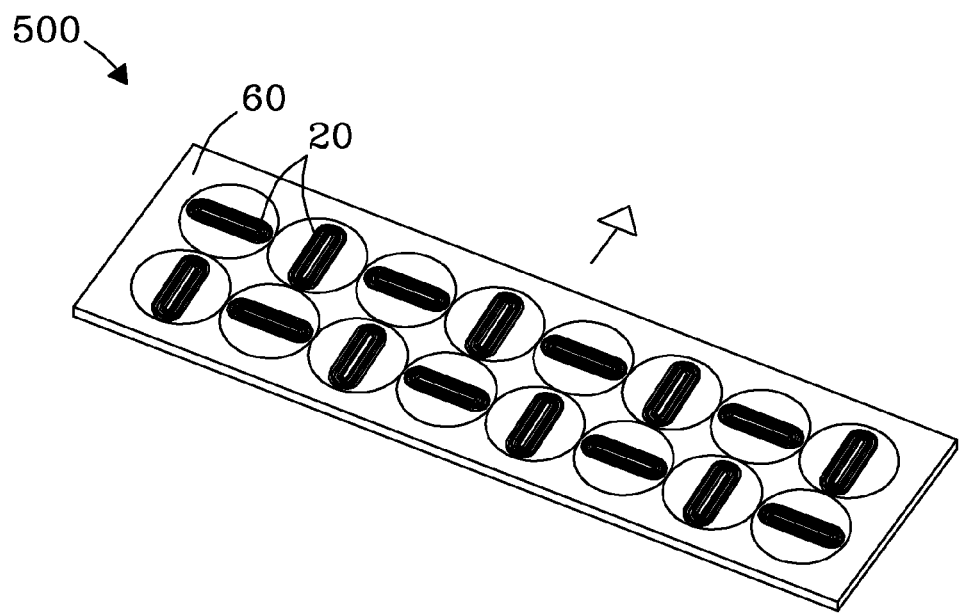
Figure 12C:
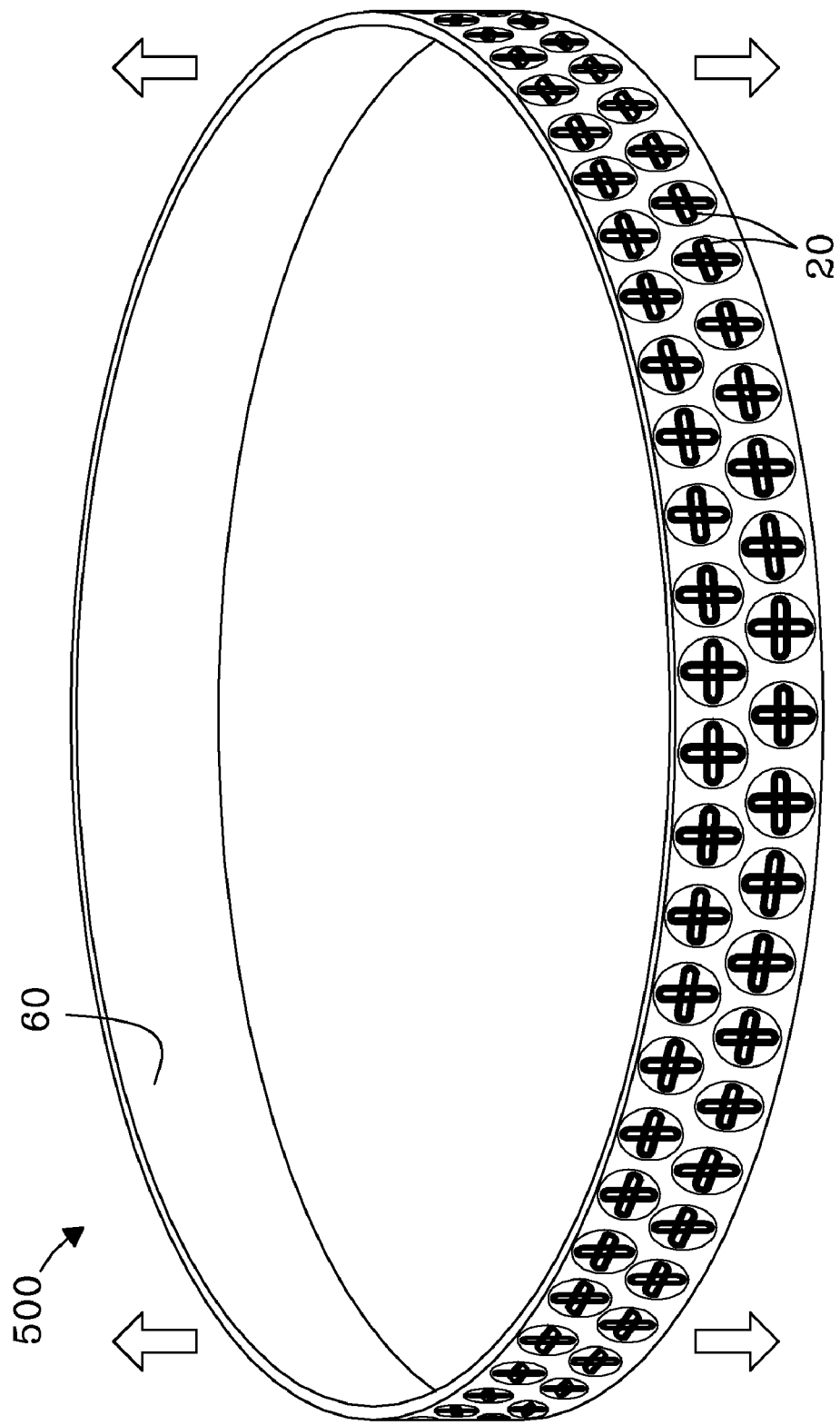

FIGS. 12*a*-12*c* illustrate three exemplary designs of a structured sensor array device 500, according to different embodiments of the invention. Each array design incorporates a preselected number of dual coil EMAT sensors 400, described previously herein, arranged in a different pattern. Other sensor patterns can also be used. FIG. 12*a* shows a network of sensors 400 of a dual overlapping coil design configured in a square or rectangular pattern. Sensors are electrically coupled in a flexible or semi-flexible support 60 or electrical network 60 that can be coupled to, or interfaced with switching components, measuring components, powering devices, and computers (and associated software) as detailed herein. Flexibility of the electrical support 60 allows the sensor array device 500 to be moved along or around a structure being scanned, providing a continuous and uniform scan of the entire surface of a structure. FIG. 12*b* shows a network of sensors 400 of a dual offset coil design configured in a square or rectangular pattern. Again, sensors are electrically coupled in a flexible electrical support 60 that can be coupled to, or interfaced with measuring components, powering devices, and computers, along with associated software. Flexibility of the electrical support 60 allows the sensor array device 500 to be moved along or around a structure being scanned, providing a continuous and uniform scan of the entire surface of a structure. FIG. 12*c* shows a network of sensors 400 of a dual overlapping coil design configured in a ring or circular pattern. Again, sensors are electrically coupled in a flexible electrical support 60 that can be coupled to, or interfaced with measuring components, powering devices, and computers, along with associated software. Flexibility of the electrical support 60 allows the sensor array device 500 to be moved along or around a structure being scanned, providing a continuous and uniform scan of the entire surface of a structure. Design patterns are not limited to the exemplary patterns. For example, sensor placement and patterns in the arrays can include a variety of shapes including, but not limited to, e.g., square, rectangle; circle, oval, rings, triangle, trapezoid, parallelogram; pentagon; hexagon; octagon; diamond; and other patterns. Structured arrays can also be used to scan an entire structure or a selected portion of an interior or exterior surface of a preselected structure including, e.g., ship hulls; fuselages, tanks, bridges, and other continuous structures as well as metal I-beams, metal trusses, and other support structures. Applications are not intended to be limiting. In addition, one or more arrays may be coupled to scan various portions or sections of a structure in a single scan. Patterns and orientations are not limited. The following examples are provided.

EXAMPLE 1

Nondestructive Examination (NDE) Measurements of a Bulged Pipeline

Scanning measurements were collected for a 20" diameter natural gas pipeline removed from service after a significant bulge was found. Scans were performed at several positions around the circumference. In one test, as the EMAT scanned the pipeline, time (i.e., time-of-flight) required for shear waves to traverse the thickness of the pipeline several times was determined every 0.1 inches along the axis of the pipeline. Spot measurements were also performed using time of flight of the shear waves to measure scanning effects when determining shear wave birefringence.

EXAMPLE 2

NDE Measurements and Assessment of Damaged Pipelines Along a Fault

Ultrasonic measurements of the strain (due to bending) were collected on bent pipelines replacing a section of a natural gas pipeline which crossed an earthquake fault in the San Francisco Bay Area (California, USA). Data collected on straight and bent pipelines provided useful data for determining the precision, accuracy, and minimum detectable strain levels. Critical baseline measurements were obtained on bent pipelines prior to installation of the replacement pipelines, thus allowing for future assessment of the integrity of the pipeline should subsequent earth movements be detected along the fault. Thirteen 40 foot sections of X60/X65 pipeline were available for testing at the fault crossing work site. Pipelines were nominally 40 feet long, 36" in diameter and ½" thick. Ultrasonic measurements were collected on 5 straight pipelines. Pipeline ends were labeled "A" and "B". Scans were started from end "B" and ended at end "A". The EMAT sensor scanned the axis of the pipelines along four lines corresponding to 90°, 180°, 270° and 360° in the positive direction relative to a weld location. As the EMAT sensor scanned along the pipelines, the time to traverse the thickness of the pipeline was recorded every 0.09". Multiple scans were performed along each line to determine precision of the ultrasonic measurements. Time of flight values were measured with a high degree of precision, to within 0.5% of the average. Variability was attributed to physical positioning and variation in the thickness and material properties of the pipeline from location to location.

EXAMPLE 3

NDE Measurements of Dented Pipelines

Dented pipelines were scanned under remote control along the axis of the pipeline from the interior. Pipeline was scanned from the interior along the axis utilizing the non-contact EMAT sensor in the motorized cart configuration. Preferred speeds were greater than 2" per second, but are not limited thereto. The EMAT generated a wave which traveled through the thickness of the pipeline every 0.2" along the axis of the pipeline as the sensor was moved continuously along the pipeline. Data were collected every 0.2" along the axis length, but again are not limited thereto.

EXAMPLE 4

Sensor Configuration and Speed of Measurement

Conventional static measurements were collected under static continuous scanning conditions every 1.5 inches along a 40 foot pipeline at a rate of approximately 2 minutes per measurement location. This corresponds to a scan time of 10.7 hours incorporating 320 measurement locations along the length of the pipeline. Continuous scanning measurements were also collected under continuous scanning conditions along the same 40 foot section of pipeline. Scanning data were collected using the scanning device and system every 0.1 inches at a speed of 5 inches per second. Two scans were used to acquire data for both wave polarizations, resulting in a scanning time of 3 minutes, which produced 4800 data points located 0.1" apart. Result was a faster scan time and an overlap in position for spatial averaging. Scanning speed can be increased by a factor of two by simply employing two EMATs with shear waves polarized at each of the two material symmetry axis. Scanning a pipeline along several lines can be accomplished by either moving the sensor along the circumference of the pipeline or laterally on a structure, e.g., by employing array systems.

CONCLUSIONS

The invention permits the severity of damage in a structure to be assessed. Results presented herein show that ultrasonic measurements can accurately assess damage in various structures, including pipelines. Estimates of strain provided by the invention can be utilized to determine structural fitness for service. The invention provides structural damage measurements that answer the question "Is the component fit for continued service at the current capacity, or does the capacity of the component need to be reduced, or do repairs need to be made immediately?" Ultrasonic measurements are sensitive to the degree of stress and strain and have shown the ability to predict strain in bulged sections. These sensors and electronics can be configured for assessment of small pipelines (~4" diameter) and are conducive for attaching to PIGs and robots that can be used to detect corrosion and stress corrosion cracking. Results also demonstrate strain in bent, bulged, and dented pipelines and structures can be detected, classified, and characterized in the field as needed. Measurements have been collected using remote motorized control from either the inside or outside of the structure to assess integrity. Integration of nondestructive determination of structural damage and computational mechanics models can be used to predict operating parameters (e.g., maximum operating pressure) for decision making regarding whether to replace or repair a damaged structure or a portion thereof. Blind field test results detected and classified severity of dents in natural gas pipelines. Results detected 100% of hidden dents and accurately determined severity in 7 of 9 hidden dents. Pressure test results on a bulged pipeline showed a direct relationship between strain predicted from nondestructive ultrasonic measurements and strain determined from dimensional measurements.

While the foregoing description has been provided, it is to be distinctly understood that the description provided above is merely an illustrative implementation of one embodiment of the present invention which is set forth below in the claims.

We claim:

1. A method for determining degree of deformation in a structure, comprising the steps of:
    determining a first polarization direction and a second polarization direction of acoustic wave travel in said structure;
    propagating and receiving test waves along a length of said structure oriented in said first and said second directions;
    plotting preselected data related to said test waves;
    calculating a birefringence value(s) from any of said propagated test waves;
    determining a strain value(s);
    plotting said strain value(s) and said birefringence value(s) to create a strain-birefringence plot;
    fitting an appropriate regression line to said strain-birefringence plot; and
    predicting strain-based deformation to said structure by comparing said plots with a baseline on said first plot.

2. The method of claim 1, wherein the step of determining said first polarization direction and said second polarization direction of acoustic wave travel includes locating the orientation of principle axes of materials in said structure being scanned.

3. The method of claim 1, wherein the step of determining a strain value includes calculating a thickness based upon said preselected data received from said test waves.

4. The method of claim 1, wherein said strain value is determined using measurements for the thickness and the circumference.

5. The method of claim 1, wherein said strain value is determined using measurements for the thickness and the size of a plate, an I-beam, or a metal component.

6. The method of claim 1, wherein said $1^{st}$ and $2^{nd}$ directions are the hoop and the axial directions, respectively, or vice versa.

7. The method of claim 1, wherein said strain is a calibration strain determined from a finite element model.

8. The method of claim 1, wherein said strain is determined by applying variables and said preselected data corresponding to said test waves using a preselected Kobayashi equation or theorem.

9. A method for determining deformation in a pipeline, the method comprising the steps of:
    determining a fast polarization direction and a slow polarization direction of acoustic travel along the pipeline relative to a pipeline axis of symmetry, wherein the acoustic travel along the fast and slow polarization directions are obtained by performing a rotation scan at several locations along the pipeline to determine the materials symmetry axis (fast and slow directions) relative to pipeline symmetry (axial and hoop);
    obtaining baseline characteristics of an undamaged portion of the pipeline;
    propagating and receiving test waves at predetermined angles at preselected locations along a length of the pipeline;
    adjusting timing width as a signal moves along pipeline to account for variations in pipeline material thickness;
    plotting a time-of-flight and a distance for said test waves;
    calculating a thickness of the pipeline based upon the time of flight value;
    calculating a birefringence of the propagated test wave;
    calculating a birefringence moving average;
    determining a strain on the pipeline from a finite element model, or data, or a mechanical engineering method;
    plotting the strain and the birefringence to create a strain-birefringence plot;
    fitting an appropriate curve to said strain-birefringence plot from the baseline obtained from the first plot; and
    predicting strain of the pipeline by comparing a measured birefringence value to a point along the fitted strain-birefringence plot.

* * * * *